United States Patent
Kearns et al.

(10) Patent No.: US 12,383,673 B2
(45) Date of Patent: *Aug. 12, 2025

(54) SYSTEMS AND METHODS FOR AUTOMATED INSULIN DELIVERY FOR DIABETES THERAPY

(71) Applicant: Tandem Diabetes Care, Inc., San Diego, CA (US)

(72) Inventors: Jacob Kearns, San Diego, CA (US); Michael Michaud, San Diego, CA (US); Geoffrey A. Kruse, San Diego, CA (US); Thomas R. Ulrich, Oceanside, CA (US); Paul Harris, San Diego, CA (US); Scott Leas, San Diego, CA (US); Betsy Dokken, San Diego, CA (US); Garrett Marin, San Diego, CA (US); Nicholas Sherer, Escondido, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 18/136,278

(22) Filed: Apr. 18, 2023

(65) Prior Publication Data
US 2024/0350728 A1 Oct. 24, 2024

Related U.S. Application Data

(63) Continuation of application No. 16/952,478, filed on Nov. 19, 2020, now Pat. No. 11,654,236.
(Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *G16H 20/17* (2018.01);
(Continued)

(58) Field of Classification Search
CPC ........ A61M 5/1723; A61M 2205/3584; A61M 2205/3592; A61M 2205/505;
(Continued)

(56) References Cited

U.S. PATENT DOCUMENTS

| 4,403,984 A | 9/1983 | Ash |
| 5,792,117 A | 8/1998 | Brown |

(Continued)

*Primary Examiner* — Jason E Flick
(74) *Attorney, Agent, or Firm* — Merchant & Gould, P.C.

(57) ABSTRACT

Disclosed herein are systems and methods for mitigating the risk of insulin stacking in automated insulin delivery systems. In AID systems configured to both automatically calculate insulin delivery based on glucose levels and receive manual programming of meal boluses configured to counteract carbohydrates in a meal, insulin stacking can result if the system automatically increases insulin delivery based on a rise in glucose levels in response to consumption of a meal and the user later programs a meal bolus for the meal. The risk of such double dosing is mitigated by the systems and methods disclosed herein by enabling the system to account for recent automated insulin increases when a meal bolus is programmed.

20 Claims, 6 Drawing Sheets

Related U.S. Application Data (60) Provisional application No. 62/939,015, filed on Nov. 22, 2019.

(51) Int. Cl.
  *A61M 5/142* (2006.01)
  *G16H 20/17* (2018.01)
  *G16H 20/60* (2018.01)

(52) U.S. Cl.
  CPC ......... *G16H 20/60* (2018.01); *A61M 2205/18* (2013.01); *A61M 2205/3584* (2013.01); *A61M 2205/3592* (2013.01); *A61M 2205/505* (2013.01); *A61M 2205/52* (2013.01); *A61M 2230/201* (2013.01)

(58) Field of Classification Search
  CPC ........ A61M 2205/52; A61M 2230/201; A61M 2205/3303; A61M 5/14244; A61M 5/142; A61M 2005/14208; A61M 5/14; A61M 5/168; A61M 5/172; A61M 2205/502; A61M 2230/20; A61M 2205/33; G16H 20/17
  See application file for complete search history.

(56) References Cited

U.S. PATENT DOCUMENTS

| | | |
|---|---|---|
| 6,068,615 A | 5/2000 | Brown et al. |
| 6,110,148 A | 8/2000 | Brown et al. |
| 6,352,523 B1 | 3/2002 | Brown et al. |
| 6,544,212 B2 | 4/2003 | Galley et al. |
| 7,060,059 B2 | 6/2006 | Keith et al. |
| 7,137,951 B2 | 11/2006 | Pilarski |
| 7,231,263 B2 | 6/2007 | Choi |
| 7,491,187 B2 | 2/2009 | Van Den Berghe et al. |
| 7,590,443 B2 | 9/2009 | Bharmi |
| 7,651,845 B2 | 1/2010 | Doyle, III et al. |
| 7,670,288 B2 | 3/2010 | Sher |
| 7,879,026 B2 | 2/2011 | Estes et al. |
| 8,088,098 B2 | 1/2012 | Yodfat et al. |
| 8,118,782 B2 | 2/2012 | Remde |
| 8,246,540 B2 | 8/2012 | Ginsberg |
| 8,452,953 B2 | 5/2013 | Buck et al. |
| 8,467,980 B2 | 6/2013 | Campbell et al. |
| 8,491,566 B2 | 7/2013 | Ramey et al. |
| 8,517,991 B2 | 8/2013 | Clemente |
| 8,545,437 B2 | 10/2013 | Sakata et al. |
| 8,552,880 B2 | 10/2013 | Kopp et al. |
| 8,556,865 B2 | 10/2013 | Krulevitch et al. |
| 8,579,879 B2 | 11/2013 | Palerm et al. |
| 8,622,991 B2 | 1/2014 | Pesach et al. |
| 8,635,054 B2 | 1/2014 | Brown |
| 8,687,811 B2 | 4/2014 | Nierzwick et al. |
| 8,818,782 B2 | 8/2014 | Thukral et al. |
| 9,089,305 B2 | 7/2015 | Hovorka |
| 9,440,025 B2 | 9/2016 | Kanderian, Jr. et al. |
| 9,477,939 B2 | 10/2016 | Brown |
| 9,486,171 B2 | 11/2016 | Saint |
| 9,486,571 B2 | 11/2016 | Rosinko |
| 9,532,737 B2 | 1/2017 | Karan et al. |
| 9,669,160 B2 | 6/2017 | Harris et al. |
| 9,757,510 B2 | 9/2017 | Finan |
| 9,833,177 B2 | 12/2017 | Blomquist |
| 9,833,571 B2 | 12/2017 | Budiman |
| 9,867,937 B2 | 1/2018 | Saint et al. |
| 9,867,953 B2 | 1/2018 | Rosinko |
| 9,937,290 B2 | 4/2018 | Connelly et al. |
| 10,016,561 B2 | 7/2018 | Saint et al. |
| 10,052,049 B2 | 8/2018 | Blomquist et al. |
| 10,569,016 B2 | 2/2020 | Rosinko |
| 10,726,100 B2 | 7/2020 | Blomquist et al. |
| 10,872,102 B2 | 12/2020 | Wei et al. |
| 10,943,687 B2 | 3/2021 | Blomquist |
| 10,966,608 B2 | 4/2021 | Bergstrom et al. |
| 11,024,429 B2 | 6/2021 | Patek et al. |
| 11,097,051 B2 | 8/2021 | Wu et al. |
| 11,116,900 B2 | 9/2021 | Haider et al. |
| 11,116,901 B2 | 9/2021 | Harris |
| 11,189,373 B2 | 11/2021 | Schmidt et al. |
| 11,217,339 B2 | 1/2022 | Blomquist |
| 11,224,693 B2 | 1/2022 | Ulrich et al. |
| 11,246,986 B2 | 2/2022 | Wilinska et al. |
| 11,291,763 B2 | 4/2022 | Blomquist et al. |
| 11,376,362 B2 | 7/2022 | Mazlish |
| 11,464,908 B2 | 10/2022 | Michaud et al. |
| 11,607,492 B2 | 3/2023 | Rosinko et al. |
| 11,654,236 B2 | 5/2023 | Kearns et al. |
| 11,676,694 B2 | 6/2023 | Kruse et al. |
| 11,749,410 B2 | 9/2023 | Hayter et al. |
| 11,751,779 B2 | 9/2023 | Kovatchev et al. |
| 2003/0100863 A1 | 5/2003 | Shekalim |
| 2003/0212379 A1 | 11/2003 | Bylund et al. |
| 2005/0065760 A1 | 3/2005 | Murtfeldt et al. |
| 2006/0132292 A1 | 6/2006 | Blomquist |
| 2006/0276771 A1 | 12/2006 | Galley et al. |
| 2007/0179434 A1* | 8/2007 | Weinert ................ G16H 20/10 600/504 |
| 2008/0071580 A1 | 3/2008 | Marcus et al. |
| 2008/0171967 A1 | 7/2008 | Blomquist et al. |
| 2008/0172027 A1 | 7/2008 | Blomquist |
| 2008/0172030 A1 | 7/2008 | Blomquist |
| 2009/0036753 A1 | 2/2009 | King |
| 2010/0145262 A1 | 6/2010 | Bengtsson et al. |
| 2010/0262117 A1 | 10/2010 | Magni et al. |
| 2010/0331652 A1 | 12/2010 | Groll et al. |
| 2011/0071464 A1 | 3/2011 | Palerm |
| 2011/0098548 A1 | 4/2011 | Budiman et al. |
| 2011/0205065 A1 | 8/2011 | Strachan et al. |
| 2012/0245556 A1 | 9/2012 | Kovatchev et al. |
| 2013/0110552 A1 | 5/2013 | Horiguchi et al. |
| 2014/0333438 A1 | 11/2014 | Halff |
| 2015/0119805 A1 | 4/2015 | Blomquist |
| 2017/0035962 A1 | 2/2017 | Lecanu-Fayet et al. |
| 2017/0189614 A1* | 7/2017 | Mazlish ............... A61M 5/1723 |
| 2018/0154077 A1 | 6/2018 | Davidson et al. |
| 2018/0296757 A1* | 10/2018 | Finan ................... G16H 20/17 |
| 2019/0019571 A1 | 1/2019 | Breton et al. |
| 2019/0099551 A1* | 4/2019 | Yodfat ............. A61M 5/16831 |
| 2019/0125969 A1 | 5/2019 | Montgomery et al. |
| 2020/0368430 A1 | 11/2020 | Ulrich et al. |
| 2021/0001044 A1 | 1/2021 | Michaud et al. |
| 2021/0038134 A1 | 2/2021 | Steil et al. |
| 2021/0113766 A1 | 4/2021 | Kearns et al. |
| 2021/0313036 A1 | 10/2021 | Breton et al. |
| 2021/0353857 A1 | 11/2021 | Ulrich et al. |
| 2022/0047812 A1 | 2/2022 | Budiman et al. |
| 2022/0062553 A1 | 3/2022 | Constantin et al. |
| 2022/0101978 A1 | 3/2022 | Blomquist |
| 2022/0233772 A1 | 7/2022 | Ulrich et al. |
| 2022/0233773 A1 | 7/2022 | Rueda et al. |
| 2022/0265927 A1 | 8/2022 | Harris et al. |
| 2023/0001090 A1 | 1/2023 | Sloan et al. |
| 2023/0034408 A1 | 2/2023 | Nichols et al. |
| 2023/0037465 A1 | 2/2023 | Rueda et al. |
| 2023/0040677 A1 | 2/2023 | Tran et al. |
| 2023/0113755 A1 | 4/2023 | Lu et al. |
| 2023/0148019 A1 | 5/2023 | Boss et al. |
| 2023/0166037 A1 | 6/2023 | Ulrich et al. |
| 2023/0277761 A1 | 9/2023 | Saint |

\* cited by examiner

SYSTEMS AND METHODS FOR AUTOMATED INSULIN DELIVERY FOR DIABETES THERAPY

RELATED APPLICATION

This application is a continuation of application Ser. No. 16/952,478, filed Nov. 19, 2020, which claims the benefit of U.S. Provisional Application No. 62/939,015, filed Nov. 22, 2019, each of which is hereby fully incorporated herein by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices that can provide continuous subcutaneous insulin injection and/or infusion therapy as an alternative to multiple daily insulin injections via syringe or injector pen. Such ambulatory infusion pumps may be worn by the user, may use replaceable medicament cartridges, and may deliver other medicaments alone, or in combination with insulin. Such medicaments include glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as continuous glucose monitoring (CGM) devices. A CGM device consists of a sensor placed under the patient's skin and affixed to the patient via an adhesive patch, a transmitter, and a monitor. A CGM device samples the patient's interstitial fluid periodically (e.g. once every 1-5 minutes) to estimate blood glucose levels over time. CGMs are advantageous because they provide more frequent insights into a user's blood glucose levels yet do not require a finger stick each time a reading is taken.

Ambulatory infusion pumps may incorporate a CGM within the hardware of the pump or may communicate with a dedicated CGM directly via a wired connection or indirectly via a wireless connection using wireless data communication protocols to communicate with a separate device (e.g., a dedicated remote device or a smartphone). One example of integration of ambulatory infusion pumps with CGM devices is described in U.S. Patent Publication No. 2014/0276419, which is hereby incorporated by reference herein. Ambulatory infusion pumps typically allow the user or caregiver to adjust the amount of insulin or other medicament delivered by a basal rate or a bolus, based on blood glucose data obtained by a CGM device, and in some cases include the capability to automatically adjust such medicament delivery. For example, based on CGM readings, some ambulatory infusion pumps may automatically adjust or prompt the user to adjust the level of medicament being administered or planned for administration or, in cases of abnormally low blood glucose readings, reducing or temporarily ceasing insulin administration.

In some cases, ambulatory insulin pumps may be configured to deliver insulin based on CGM data in a closed-loop or semi-closed-loop fashion. Some systems including these features may be referred to as automated insulin delivery (AID) systems or artificial pancreas systems because these systems serve to mimic biological functions of the pancreas for persons with diabetes.

Some AID systems primarily deliver medicament automatically based on CGM readings, but also enable users to program meal boluses. Consumption of carbohydrates in a meal causes blood glucose to rise, which can be counteracted by insulin or other medicament delivered in a meal bolus. If a user delays in delivering the meal bolus, the user's blood glucose may begin to rise prior to the meal bolus being delivered. This can be problematic with AID systems that automatically deliver correction boluses (and/or increase a basal rate) based on CGM readings, because the system may deliver a correction bolus in response to the CGM readings and the user then subsequently delivers a meal bolus. This "insulin stacking" resulting from two separate insulin deliveries intended to counteract the same rise in blood glucose can cause the user's blood glucose to drop to a low level.

SUMMARY OF THE INVENTION

Disclosed herein are systems and methods for mitigating the risk of insulin stacking in automated insulin delivery systems. In AID systems configured to both automatically calculate insulin delivery based on glucose levels and receive manual programming of meal boluses configured to counteract carbohydrates in a meal, insulin stacking can result if the system automatically increases insulin delivery based on a rise in glucose levels in response to consumption of a meal and the user later programs a meal bolus for the meal. The risk of such double dosing is mitigated by the systems and methods disclosed herein by enabling the system to account for recent automated insulin increases when a meal bolus is programmed.

In an embodiment, an ambulatory infusion pump system can include a pump mechanism configured to facilitate delivery of insulin to a user, a user interface, a communications device adapted to receive glucose levels from a continuous glucose monitor and a processor functionally linked to the pump mechanism, the user interface and the communications device. The processor can be configured to automatically calculate insulin doses with a closed loop delivery algorithm based on glucose levels received from the continuous glucose monitor. If user input is received through the user interface programming a meal bolus configured to deliver insulin to counteract carbohydrates consumed in a meal, the processor can determine if the meal bolus is programmed within a predetermined time of one or more automatically calculated insulin doses that increased an amount of insulin delivered to the user. The processor can then automatically modify the meal bolus if the meal bolus was programmed within the predetermined time of the automatically calculated insulin dose that increased the amount of insulin delivered to the user in order to reduce the possibility of insulin stacking.

In an embodiment, an ambulatory infusion pump system can include a pump mechanism configured to facilitate delivery of insulin to a user, a user interface, a communications device adapted to receive glucose levels from a continuous glucose monitor and a processor functionally linked to the pump mechanism, the user interface and the communications device. The processor can be configured to receive user input through the user interface programming a meal bolus configured to deliver insulin to counteract carbohydrates consumed in a meal. The processor can then determine if a closed loop delivery algorithm calculated an increase in insulin based on glucose levels received from the continuous glucose monitor that was delivered within a predetermined time prior to programming of the meal bolus. The processor can automatically modify the meal bolus if the increase in insulin based on glucose levels received from the continuous glucose monitor was delivered within the predetermined time prior to programming of the meal bolus to reduce the possibility of insulin stacking.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
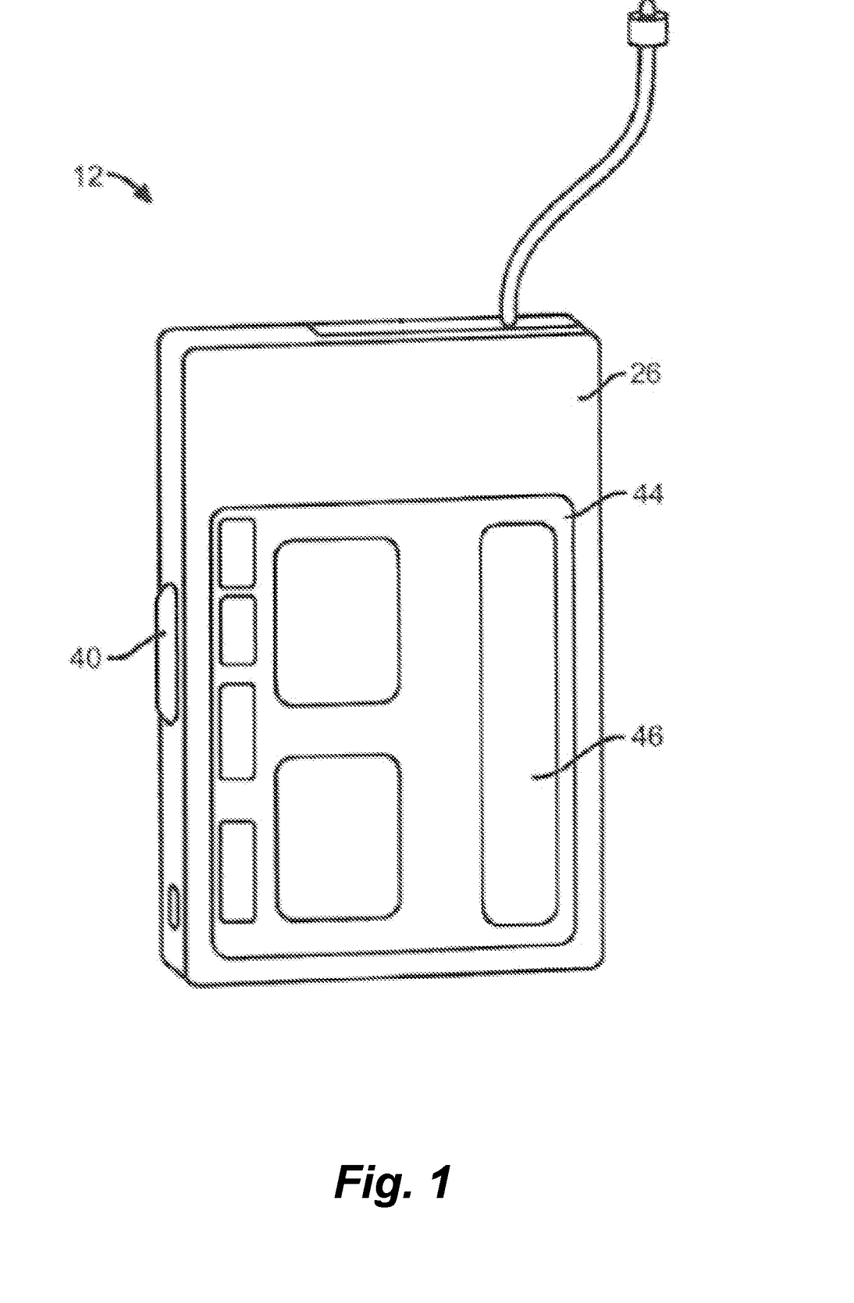
FIG. 1 is an embodiment of an ambulatory infusion pump for use with embodiments of the disclosure.

FIG. 1 depicts an example infusion pump that can be used in conjunction with one or more embodiments of the ambulatory infusion pump system of the present disclosure. Pump 12 includes a pumping or delivery mechanism and reservoir for delivering insulin or other medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display (e.g., a dedicated remote display or a CGM display), a remote control device, or a consumer electronic device (e.g., laptop computer, personal computer, tablet computer, smartphone, electronic watch, electronic health or fitness monitor, or personal digital assistant). Further details regarding such pump devices can be found in U.S. Pat. No. 8,287,495, previously incorporated by reference above. It is to be appreciated that pump 12 may be optionally configured to deliver one or more additional or other medicaments to a patient.

Figure 2:
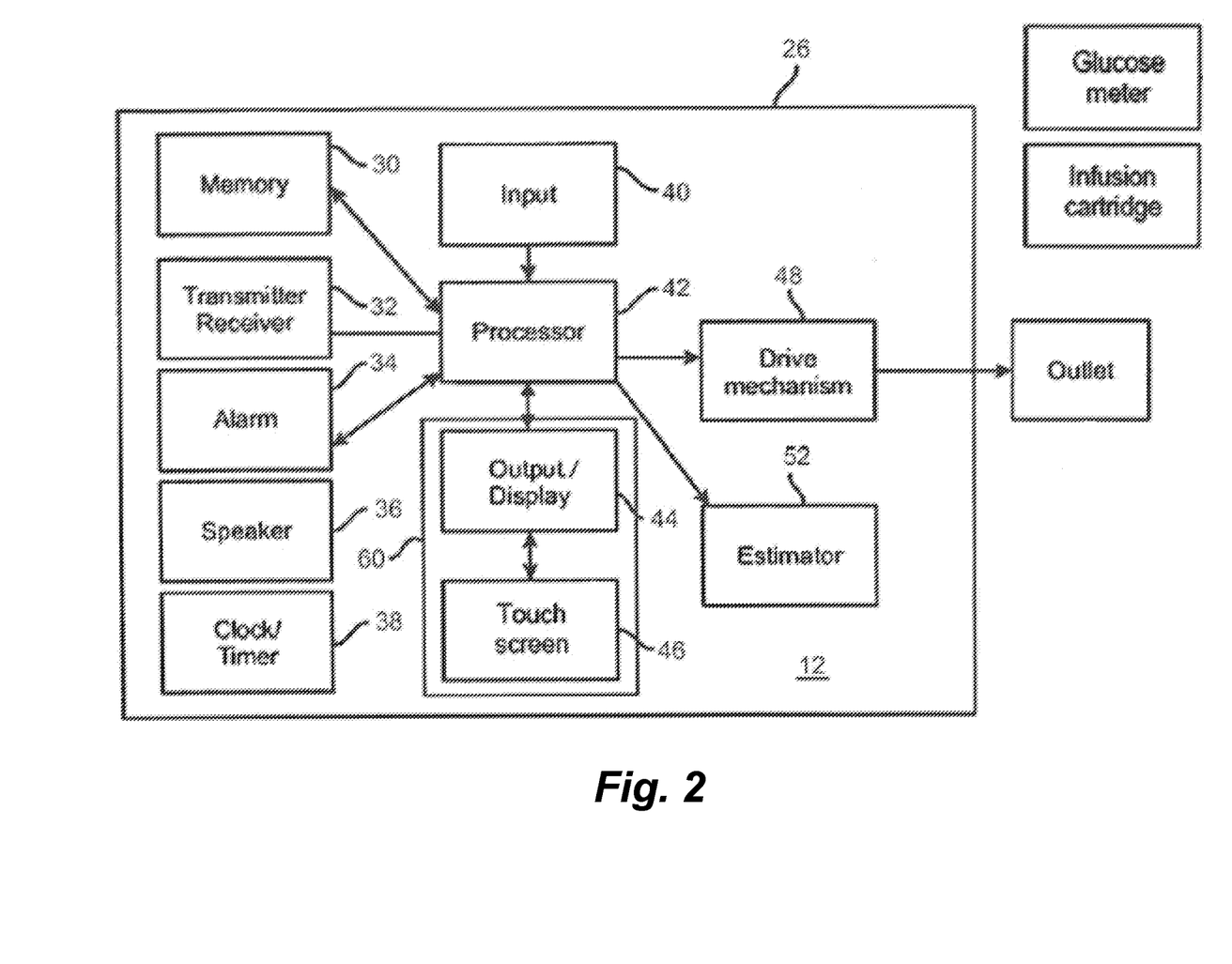
FIG. 2 is a block diagram of the ambulatory infusion pump of FIG. 1.

FIG. 2 illustrates a block diagram of some of the features that may be included within the housing 26 of pump 12. The pump 12 can include a processor 42 that controls the overall functions of the pump. The pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices through the transmitter/receiver 32 such as a remote device (e.g., CGM device), a remote control device, or a consumer electronic device (e.g., laptop computer, personal computer, tablet computer, smartphone, electronic watch, electronic health or fitness monitor, or personal digital assistant). In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. The processor 42 may also include programming to receive signals and/or other data from an input device, such as, by way of example, a pressure sensor, a temperature sensor, or the like.

Figure 3A:
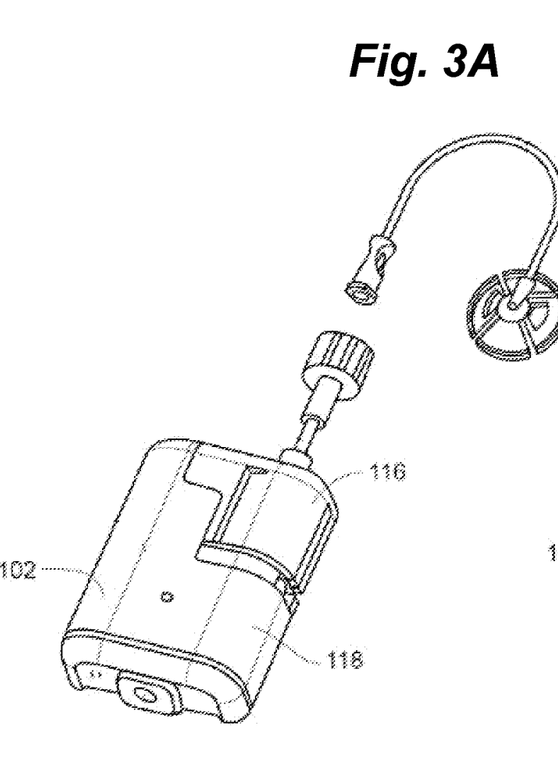
FIGS. 3A-3B are an alternate embodiment of an ambulatory infusion pump for use with embodiments of the disclosure.
Figure 3B:
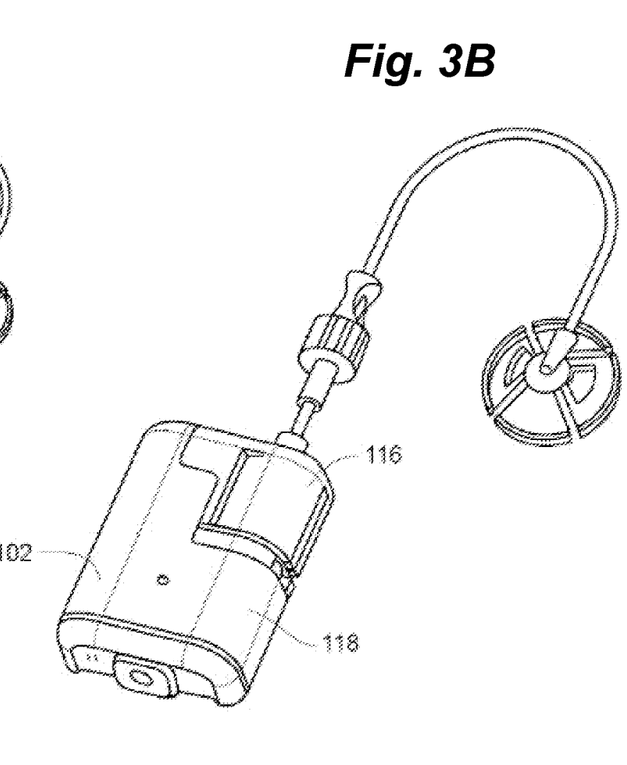

FIGS. 3A-3B depicts a second infusion pump that can be used in conjunction with one or more embodiments of the ambulatory infusion pump system of the present disclosure. Pump 102 includes a pump drive unit 118 and a medicament cartridge 116. Pump 102 includes a processor that may communicate with one or more processors within the pump 102 and/or one or more processors of other devices such as a remote device (e.g., a CGM device), a remote control device, or a consumer electronic device (e.g., laptop computer, personal computer, tablet computer, smartphone, electronic watch, electronic health or fitness monitor, or personal digital assistant). The processor 42 may also include programming to receive signals and/or other data from an input device, such as, by way of example, a pressure sensor, a temperature sensor, or the like. Pump 102 also includes a processor that controls some or all of the operations of the pump. In some embodiments, pump 102 receive commands from a separate device for control of some or all of the operations of the pump. Such separate device can include, for example, a dedicated remote control device or a consumer electronic device such as a smartphone having a processor executing an application configured to enable the device to transmit operating commands to the processor of pump 102. In some embodiments, processor can also transmit information to one or more separate devices, such as information pertaining to device parameters, alarms, reminders, pump status, etc. Such separate device can include any remote display, remote control device, or a consumer electronic device as described above. Pump 102 can also incorporate any or all of the features described with respect to pump 12 in FIG. 2. In some embodiments, the communication is effectuated wirelessly, by way of example only, via a near field communication (NFC) radio frequency (RF) transmitter or a transmitter operating according to a "Wi-Fi" or Bluetooth® protocol, Bluetooth® low energy protocol or the like. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
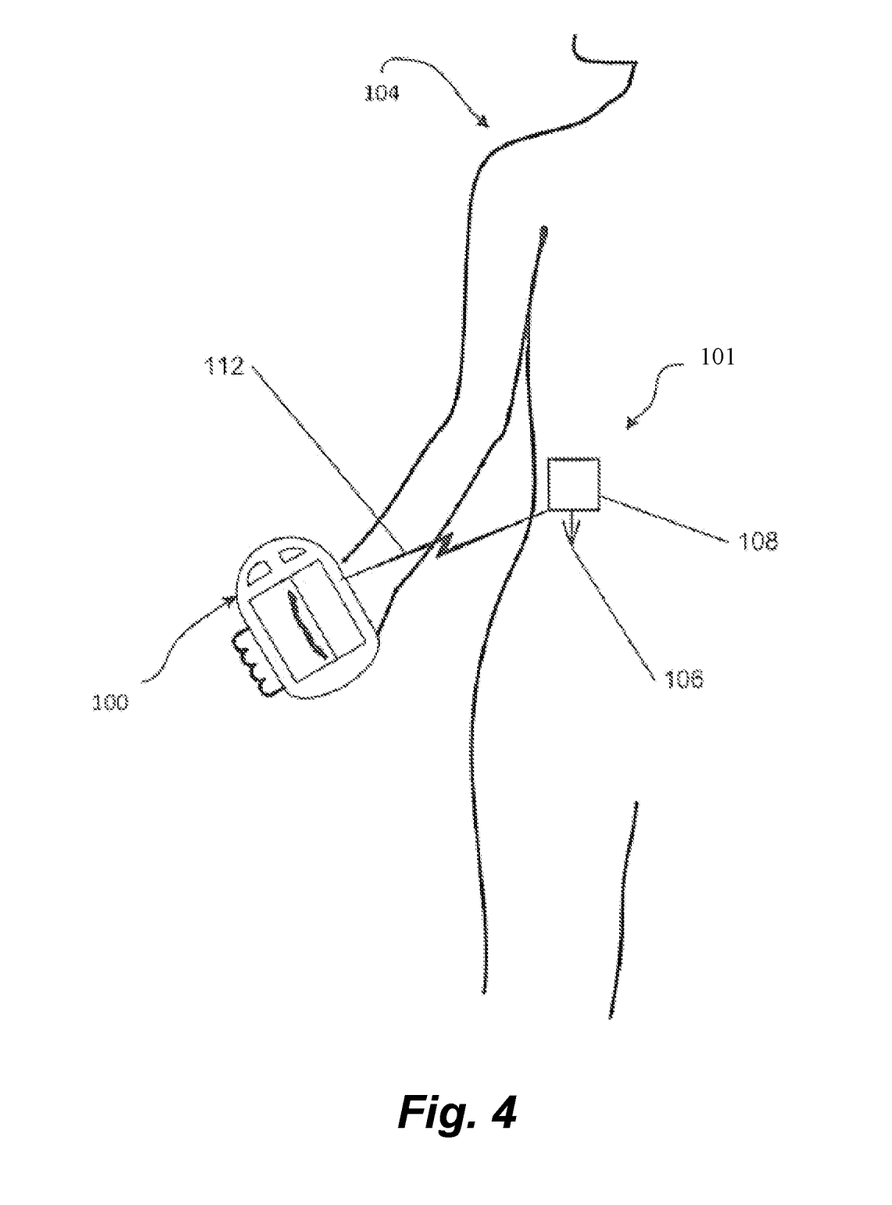
FIG. 4 is an embodiment of a CGM for use with embodiments of the disclosure.

FIG. 4 depicts an example CGM system that can be used in conjunction with one or more embodiments of the ambulatory infusion pump system of the present disclosure. The CGM system includes a sensor 101, a sensor probe 106, a sensor body 108, a receiver, and a monitor (receiver and monitor are depicted as device 100 in FIG. 4). The sensor 101 is removably affixed to a user 104 and includes a sensor probe 106 configured for transcutaneous insertion into the user 104. When placed, the sensor probe 106 reacts with the user's interstitial fluid which produces a signal that can be associated with the user's blood glucose level. The sensor 101 further includes a sensor body 108 that transmits data associated with the signal to the receiver 100 via wired or wireless connection (as represented by arrow line 112). In preferred embodiments, the receiver 100 receives the transmitted data wirelessly by any suitable means of wireless communication. By way of example only, this wireless communication may include a near field communication (NFC) radio frequency (RF) transmitter or a transmitter operating according to a "Wi-Fi" or Bluetooth® protocol, Bluetooth® low energy protocol or the like. Further detail regarding such systems and definitions of related terms can be found in, e.g., U.S. Pat. Nos. 8,311,749, 7,711,402 and 7,497,827, each of which is hereby incorporated by reference in its entirety.

With the infusion pump and CGM interfaced, the CGM can automatically transmit the CGM data to the pump. The pump can then use this data to automatically determine therapy parameters and suggest a therapy adjustment to the user or automatically deliver the therapy adjustment to the user. These therapy parameters including thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

For example, if the CGM readings indicate that the user has or is predicted to have a high blood glucose level (hyperglycemia), the ambulatory infusion system can automatically calculate an insulin dose sufficient to reduce the user's blood glucose level below a threshold level or to a target level and automatically deliver the dose. Alternatively, the ambulatory infusion system can automatically suggest a change in therapy upon receiving the CGM readings such as an increased insulin basal rate or delivery of a bolus, but can require the user to accept the suggested change prior to delivery rather than automatically delivering the therapy adjustments.

By way of further example, if the CGM readings indicate that the user has or is predicted to have a low blood glucose level (hypoglycemia), the ambulatory infusion system can, for example, automatically reduce or suspend a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the patient address the hypoglycemic condition as necessary (e.g., ingest carbohydrates), singly or in any desired combination or sequence. Such determination can be made by the infusion pump providing therapy or by a separate device that transmits therapy parameters to the infusion pump. In some embodiments, multiple medicaments can be employed in such an ambulatory infusion system as, for example, a first medicament, e.g., insulin, that lowers blood glucose levels and a second medicament, e.g., glucagon, that raises blood glucose levels.

Automated insulin delivery (AID) systems such as those described above can also enable a user to manually program meal boluses of insulin or other medicaments to counteract the rise in blood glucose caused by the consumption of carbohydrates. However, as noted above this can result in "insulin stacking" in such systems if the user delays programming of the meal bolus and the AID system first delivers a correction bolus and/or increases a basal rate in response to the rise in blood glucose caused by the carbohydrates and the user then subsequently programs the meal bolus. Embodiments herein therefore seek to minimize the risk and effect of such insulin stacking and the corresponding risk of dangerously low blood glucose levels.

In embodiments, an AID system can include auto-correction bolus logic that considers insulin or insulin on board from recent automated correction boluses and/or increased basal rates above the open-loop basal rate when calculating meal boluses. In such an embodiment, a meal bolus programmed within a predetermined time of an automated insulin increase is reduced by a predetermined amount based on the previous increase. In embodiments, the predetermined time can be one hour and the decrease can be any percentage of the automated insulin increase (0% to 100%). Such a meal bolus could therefore be calculated according to one or more of equation (1) or equation (2) below, depending on the type of insulin increase:

Meal bolus=(grams of carbohydrates/carbohydrate ratio)−(0-100%*(automated correction bolus value(s) delivered within the past hour));  (1)

Meal bolus=(grams of carbohydrates/carbohydrate ratio)−(0-100%*(basal insulin amount above open loop profile basal rate delivered within the past hour)).  (2)

By going back in time to factor in previous increases that may have resulted from ingestion of the same carbohydrates the meal bolus is intended to counteract, the likelihood of insulin stacking is decreased. The predetermined time within which prior automated insulin deliveries are accounted for can alternatively be a time greater than or less than one hour in various embodiments, such, as for example, 15 minutes, 30 minutes, 45 minutes, 1.5 hours, etc. In some embodiments, the percentage of the automated insulin increase by which the meal bolus is decreased can vary by the amount of time that has elapsed since the automated insulin delivery such that when an automated insulin delivery was made more recently a higher percentage of the delivery is reduced from the meal bolus. For example, in one non-limiting example, if an automatic correction bolus was delivered an hour ago, the meal bolus can be reduced by 25% of the correction bolus whereas if the correction bolus was delivered a half hour ago, the meal bolus can be reduced by 50% given the higher likelihood that a more recent bolus may have resulted from consumption of the meal.

In some embodiments, the decrease in a meal bolus programmed within a predetermined amount of time of an automated insulin delivery increase can further take into account any glucose that would have been burned by insulin independent or insulin dependent pathways over the time since the meal was consumed by utilizing an insulin-on-board decay curve. One example equation that could be employed in such an embodiment is set forth in equation (3) below.

$$\text{Meal bolus}=(\text{grams of carbohydrates/carbohydrate ratio})*\text{Swan6hrIOB\_decay\_curve}(\text{time\_since\_meal})-\text{IOB} \quad (3)$$

In embodiments, the Swan6hrIOB_decay_curve (time_since_meal) value can equal 100% at time=0 minutes and can equal 0% at time=360 minutes, with a value between 0-100% being applied at all times in between 0-360 minutes based on the IOB decay curve. In such embodiments, the meal bolus value calculated by grams of carbohydrates/carbohydrate ration is reduced by an amount between 0-100 percent to account for any glucose burned by insulin independent or insulin dependent pathways since the meal. By taking account of the time food has been digesting and blood sugar that has been consumed since the meal was eaten, the likelihood of stacking insulin decreases.

Figure 5:
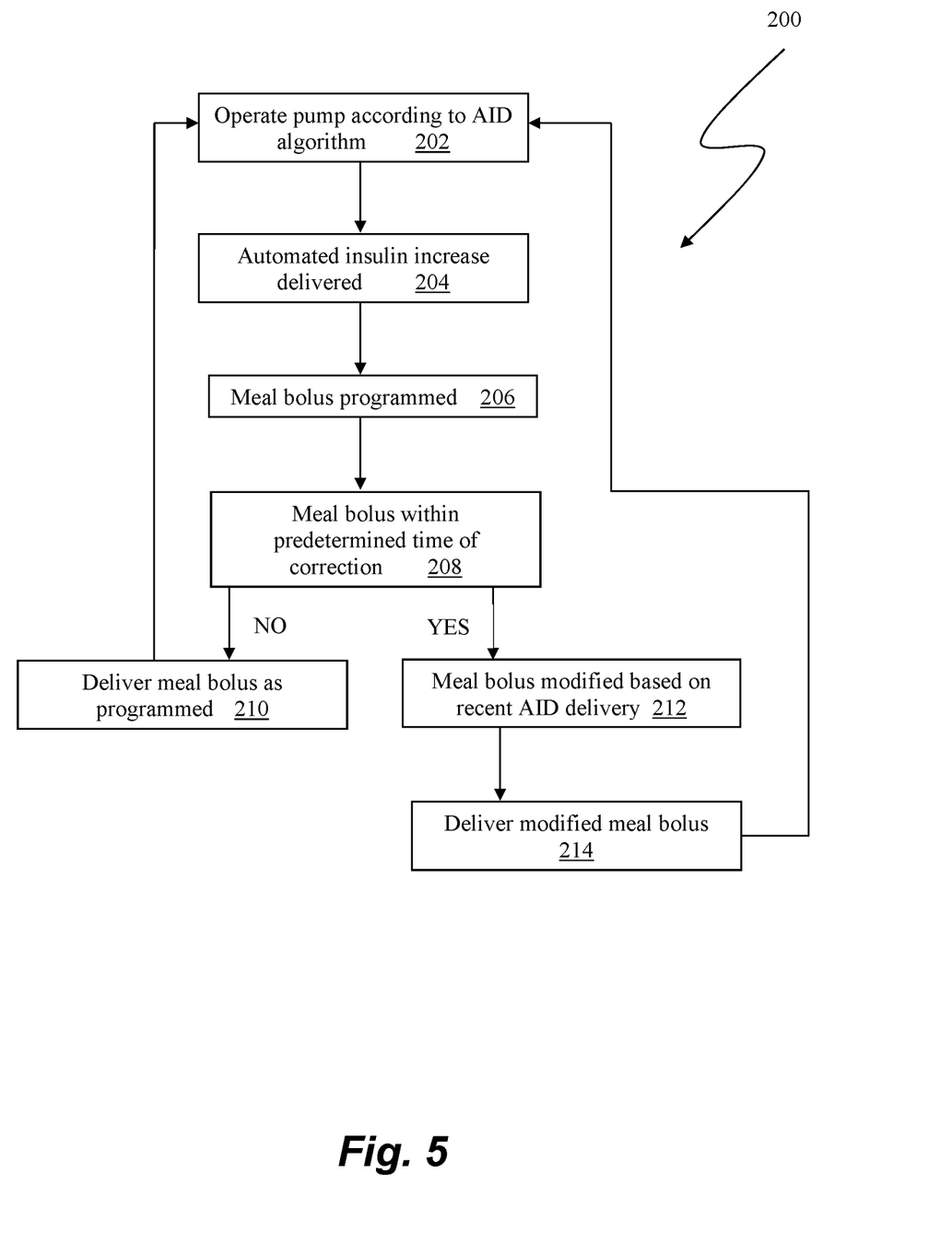
FIG. 5 is a flowchart of a method of delivering medicament in automated insulin delivery systems according to an embodiment.

Referring now to FIG. 5, a method 200 of delivering boluses in automated insulin delivery systems according to an embodiment is depicted. At step 202, the user's pump is operated according to an automated insulin delivery algorithm that automatically delivers insulin to the user based on CGM readings. Automated insulin, such as an automated correction bolus or an automated basal rate increase, is delivered to the user in response to current or predicted future glucose levels at step 204. The user then programs a meal bolus at step 206. At step 208, the system determines if the meal bolus was programmed within a predetermined time (e.g., one hour) of the most recent automated insulin delivery. If the meal bolus was not programmed within the predetermined time of the most recent automated correction bolus, the meal bolus can be delivered as programmed at step 210. If the meal bolus was programmed within the predetermined time, the meal bolus can be reduced as set forth above to account for the recent automated insulin delivery at step 212. The modified meal bolus is then delivered at step 214. Following either meal bolus delivery, the system can then resume delivery insulin according to the AID algorithm.

According to other embodiments, meal boluses programmed within a predetermined time of a previously delivered automated correction bolus can be automatically modified to be delivered over a different time period. Rather than all of the meal bolus being delivered at once, the system can deliver only a portion of the bolus such as, e.g., half of the bolus, upon execution of the bolus command and selectively delay delivery of a second portion of the bolus for a predetermined period of time. In embodiments, after the predetermined time has elapsed, the second portion of the bolus is delivered only if the predicted glucose level of the user is above a minimum threshold. For example, if a meal bolus is programmed within an hour of an automated correction bolus, the system can automatically delay a portion of the bolus for 15 minutes in order to observe the user's glucose levels prior to delivery of the second portion of the bolus. This can ensure that the second portion of the meal bolus is actually needed and the additional carbohydrates in the meal were not already addressed by the previous automated correction bolus to help prevent insulin stacking and potentially lowering the user's glucose to dangerous levels. In embodiments, various time periods can be used for both the time between the automated correction bolus and the meal bolus and the time that the second portion of the meal bolus is delayed, such as, for example, 15 minutes, 30 minutes, 45 minutes, 1 hour, etc. In various embodiments, the first and second portions of the meal bolus can be equal to the total amount of the initially programmed meal bolus or can be a reduced amount of the initially calculated meal bolus based on one or more of the factors discussed herein. In other embodiments, the entire meal bolus can be delayed.

Figure 6:
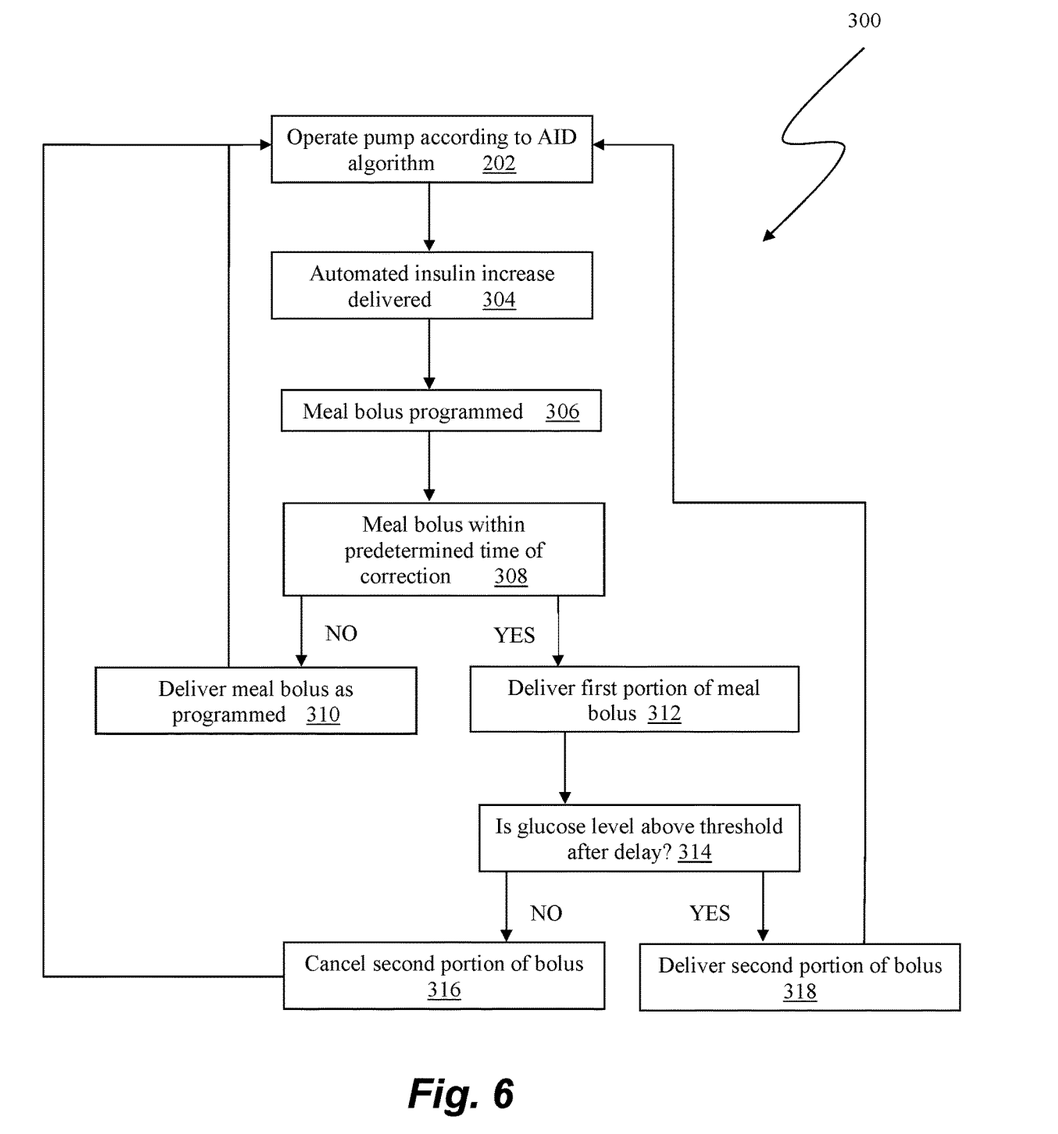
FIG. 6 is a flowchart of a method of delivering medicament in automated insulin delivery systems according to an embodiment.

Referring now to FIG. 6, a method 300 of delivering boluses in automated insulin delivery systems according to an embodiment is depicted. As with method 200 described above, the user's pump is operated according to an automated insulin delivery algorithm that automatically delivers insulin to the user based on CGM reading at step 302 and automated insulin is delivered to the user in response to current or predicted future glucose levels at step 304. After the user programs a meal bolus at step 306, the system determines if the meal bolus was programmed within a predetermined time of the most recent automated insulin delivery at step 308. If the meal bolus was not programmed within the predetermined time of the most recent automated correction bolus, the meal bolus can be delivered as programmed at step 310. If the meal bolus was programmed within the predetermined time, the meal bolus can be modified such that a first portion of the bolus is delivered at step 312. The system then waits a predetermined period of time to determine if the current or future predicted glucose level of the user is above a threshold at step 314. If the glucose level is not above the threshold, the second portion of the meal bolus is cancelled at step 316 whereas if the glucose level is above the threshold, the second portion of the meal bolus is then delivered at step 314. Following delivery of all or a portion of the meal bolus, the system can then resume delivery insulin according to the AID algorithm.

In other embodiments, when a meal bolus is programmed within a predetermined time of an automated correction bolus, rather than modifying the meal bolus the system can instead automatically modify one or more basal rates of the user. For example, the meal bolus is delivered as programmed, but the current basal rate being delivered to the user can automatically be reduced. Alternatively or additionally, a maximum basal rate that the system is allowed to determine and deliver to the user can be reduced during when and after the meal bolus is delivered. In embodiments, such reductions can be for a set period of time such as, e.g., 30 minutes, 1 hour, etc. or can be based on CGM data. For example, the basal rate can be reduced until the CGM data shows stable glucoses levels not at risk of going below a low threshold.

Although the methods described above specifically relate to a system that automatically modifies, e.g., meal boluses programmed within a predetermined time of an automated correction bolus, in other embodiments, the system may only make such modifications if the user provides input into the pump and/or remote control indicating that the user is programming the meal bolus late (i.e., at least 5 minutes after starting the meal).

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
   a pump configured to facilitate delivery of insulin to a user;
   at least one processor functionally linked to the pump, the at least one processor configured to:
   automatically calculate insulin doses with a closed loop delivery algorithm based on glucose levels of the user;
   determine that a meal bolus configured to deliver insulin to counteract carbohydrates consumed in a meal should be delivered to the user;
   determine if the determination to deliver the meal bolus is within a predetermined time of one or more automatically calculated insulin doses that increased an amount of insulin delivered to the user; and
   automatically modify the meal bolus if the determination to deliver the meal bolus was within the predetermined time of the automatically calculated insulin dose that increased the amount of insulin delivered to the user.

2. The system of claim 1, wherein the at least one processor is configured to determine that a meal bolus configured to deliver insulin to counteract carbohydrates consumed in a meal should be delivered to the user by receiving user input programming a meal bolus.

3. The system of claim 1, wherein the at least one processor is configured to cause the meal bolus to be delivered without modifying the meal bolus if the meal bolus was not determined to be delivered within the predetermined time of an automatically calculated insulin dose that increased the amount of insulin delivered to the user.

4. The system of claim 1, wherein the at least one processor is configured to automatically modify the meal bolus if the meal bolus was programmed within the predetermined time by reducing an amount of the meal bolus.

5. The system of claim 4, wherein the at least one processor is configured to reduce the amount of the meal bolus based on an amount of increase of the one or more automatically calculated insulin doses that increased the amount of insulin delivered to the user.

6. The system of claim 5, wherein the amount of increase of the one or more automatically calculated insulin doses utilized by the at least one processor includes amounts of automatic correction boluses.

7. The system of 5, wherein the amount of increase of the one or more automatically calculated insulin doses utilized by the at least one processor includes basal insulin delivery greater than an open loop basal rate profile.

8. The system of claim 5, wherein the at least one processor is configured to reduce the amount of the meal bolus by a predetermined percentage of the amount of increase of the one or more automatically calculated insulin doses that increased the amount of insulin delivered to the user.

9. The system of claim 8, wherein the predetermined percentage varies based on a time that has elapsed since the one or more automatically calculated insulin doses that increased the amount of insulin delivered to the user.

10. The system of claim 4, wherein the processor is configured to reduce the amount of the meal bolus by delivering a first portion of the meal bolus.

11. The system of claim 10, wherein the processor is configured to deliver a second portion of the meal bolus after a predetermined period of time only if a glucose level of the user is above a threshold level.

12. The system of claim 4, wherein the processor is configured to reduce the amount of the meal bolus based on an insulin decay curve that accounts for blood glucose burned in the user after the meal was consumed.

13. An ambulatory infusion pump system, comprising:
   a pump mechanism configured to facilitate delivery of insulin to a user;

at least one processor functionally linked to the pump, the at least one processor configured to:
- determine that a meal bolus configured to deliver insulin to counteract carbohydrates consumed in a meal should be delivered to the user;
- determine if a closed loop delivery algorithm calculated an increase in insulin based on glucose levels of the user that was delivered within a predetermined time prior to determining that the meal bolus should be delivered; and
- automatically modify the meal bolus if the increase in insulin based on glucose levels received from the continuous glucose monitor was delivered within the predetermined time of determining that the meal bolus should be delivered.

14. The system of claim 13, wherein the at least one processor is configured to determine that a meal bolus configured to deliver insulin to counteract carbohydrates consumed in a meal should be delivered to the user by receiving user input programming a meal bolus.

15. The system of claim 14, wherein the at least one processor is configured to automatically modify the meal bolus by reducing an amount of the meal bolus if the increase in insulin based on glucose levels received from the continuous glucose monitor was delivered within the predetermined time of determining that the meal bolus should be delivered.

16. The system of claim 15, wherein the at least one processor is configured to reduce the amount of the meal bolus based on an amount of the increase in insulin.

17. The system of claim 16, wherein the amount of the increase in insulin utilized by the at least one processor can include automatic correction boluses and basal insulin delivery greater than an open loop basal rate profile.

18. The system of claim 16, wherein the at least one processor is configured to reduce the amount of the meal bolus by a predetermined percentage of the amount of the increase in insulin.

19. The system of claim 15, wherein the at least one processor is configured to reduce the amount of the meal bolus by delivering a first portion of the meal bolus.

20. The system of claim 19, wherein the at least one processor is configured to deliver a second portion of the meal bolus after a predetermined period of time only if a glucose level of the user is above a threshold level.

* * * * *